(12) United States Patent
Chang et al.

(10) Patent No.: US 9,057,110 B2
(45) Date of Patent: *Jun. 16, 2015

(54) METHOD FOR DIRECT AMPLIFICATION FROM CRUDE NUCLEIC ACID SAMPLES

(71) Applicant: LIFE TECHNOLOGIES CORPORATION, Carlsbad, CA (US)

(72) Inventors: Chien-Wei Chang, Belmont, CA (US); Lori Hennessy, San Mateo, CA (US); Dennis Wang, Dublin, CA (US)

(73) Assignee: APPLIED BIOSYSTEMS LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/914,478

(22) Filed: Jun. 10, 2013

(65) Prior Publication Data

US 2014/0120541 A1    May 1, 2014

Related U.S. Application Data

(63) Continuation of application No. 13/438,436, filed on Apr. 3, 2012, now Pat. No. 8,460,934, which is a continuation of application No. 12/495,705, filed on Jun. 30, 2009, now Pat. No. 8,173,401.

(60) Provisional application No. 61/077,113, filed on Jun. 30, 2008.

(51) Int. Cl.
    *C12Q 1/68*     (2006.01)

(52) U.S. Cl.
    CPC ............... *C12Q 1/6888* (2013.01); *C12Q 1/68* (2013.01); *C12Q 1/6806* (2013.01); *C12Q 1/686* (2013.01)

(58) Field of Classification Search
    CPC ....................................................... C12Q 1/68
    USPC ........................................................ 435/6.1
    See application file for complete search history.

(56) References Cited

U.S. PATENT DOCUMENTS

| | | | |
|---|---|---|---|
| 5,501,963 A | 3/1996 | Burckhardt et al. | |
| 5,824,517 A | 10/1998 | Cleuziat et al. | |
| 5,837,453 A | 11/1998 | Harley et al. | |
| 5,861,251 A | 1/1999 | Park et al. | |
| 5,962,665 A | 10/1999 | Kroeger et al. | |
| 6,297,005 B1 | 10/2001 | Zhong et al. | |
| 6,803,200 B2 * | 10/2004 | Xia et al. | 435/6.12 |
| 7,008,771 B1 | 3/2006 | Schumm et al. | |
| 8,173,401 B2 * | 5/2012 | Chang et al. | 435/91.2 |
| 8,460,934 B2 * | 6/2013 | Chang et al. | 435/975 |
| 2002/0012924 A1 | 1/2002 | Schumm et al. | |
| 2003/0049614 A1 | 3/2003 | Hogrefe | |
| 2004/0053254 A1 | 3/2004 | Wangh et al. | |
| 2005/0026147 A1 | 2/2005 | Walker et al. | |
| 2006/0014185 A1 | 1/2006 | Ollikka et al. | |
| 2008/0124768 A1 | 5/2008 | Mueller et al. | |
| 2008/0138804 A1 | 6/2008 | Buzby | |
| 2009/0305899 A1 * | 12/2009 | Meegan et al. | 506/2 |
| 2010/0015621 A1 | 1/2010 | Chang et al. | |

FOREIGN PATENT DOCUMENTS

| | | |
|---|---|---|
| EP | 1050587 | 4/2007 |
| WO | 0050564 | 8/2000 |
| WO | 2006090987 | 8/2006 |
| WO | 2008002740 | 1/2008 |
| WO | 2010002938 | 1/2010 |

OTHER PUBLICATIONS

Nagai, M. et al. "Additive effects of bovine serum albumin, ithiothreitol, and glycerol on PCR," Biochemistry and Molecular Biology International, Academic Press, London, GB, vol. 44, No. 1, 1998, pp. 157-163.

Abu Al-Soud, W. et al. "Effects of amplification facilitators on diagnostic PCR in a presence of blood, feces, and meat" Journal of Clinical Microbiology, vol. 38, No. 12, 2001, pp. 4463-4470.

EP09774388.4 Extended European Search Report mailed Sep. 22, 2011.

PCT/US2009/049323 International Search Report mailed Feb. 17, 2010.

PCT/US2009/049323 International Preliminary Report on Patentability mailed Jan. 13, 2011.

* cited by examiner

*Primary Examiner* — Ardin Marschel

(57) ABSTRACT

The present teachings relate to improved methods, kits, and reaction mixtures for amplifying nucleic acids. In some embodiments a novel direct buffer formulation is provided which allows for the direct amplification of the nucleic acids in a crude sample with minimal sample purification.

5 Claims, 13 Drawing Sheets

US 9,057,110 B2

METHOD FOR DIRECT AMPLIFICATION FROM CRUDE NUCLEIC ACID SAMPLES

CROSS REFERENCE TO RELATED APPLICATIONS

This application claims priority benefit under 35 U.S. C. §119(e) from U.S. Application No. 61/077,113 filed Jun. 30, 2008, the contents of which are incorporated herein by reference.

FIELD

The present teachings generally relate to methods of directly amplifying nucleic acids from crude samples.

INTRODUCTION

Rapid and accurate detection of DNA profiles is a key aspect of forensic casework sample analysis. Crude samples such as blood and buccal swabs contain substances that can inhibit the activity of the polymerases used for PCR-based short tandem repeat (STR) typing. Historically, it has been necessary to remove inhibitors and purify DNA before performing downstream enzymatic manipulations such as PCR amplification. Many kinds of DNA isolation and purification methods and kits are commercially available. However, their use adds time and expense to the preparation of samples for subsequent analysis.

SUMMARY

The present teachings provide a method of performing a polymerase chain reaction (PCR) comprising; providing a crude sample comprising: deoxyribonucleic acid; optionally incubating the crude sample with NaOH at 5 mM to 25 mM; mixing the crude sample with a direct buffer to form a nucleic acid containing solution; and performing a PCR on the deoxyribonucleic acid, wherein the direct buffer comprises at least 3%-8% glycerol, 0.2%-0.9% non-ionic surfactants, and 1000-3000 ug/ml BSA. Suitable non-ionic surfactants include, but not limited to, polysorbate (Tween), Tween 20, Triton-X 100 and the like.

The present teachings provide methods of performing a polymerase chain reaction (PCR) comprising; providing a crude sample comprising: deoxyribonucleic acid; optionally incubating the crude sample with NaOH at 5 mM to 25 mM; mixing the crude sample with a direct buffer to form a nucleic acid containing solution; and performing PCR on the solution, wherein the direct buffer comprises at least 5 PCR primer pairs, 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% polysorbate, 1000-3000 ug/ml BSA, and 0.10-0.35 U/ul of DNA polymerase.

In some embodiments, the present teachings provide methods of determining the identity of a human comprising; providing a crude sample comprising deoxyribonucleic acid from the human; optionally incubating the crude sample with NaOH at 5 mM to 25 mM; mixing the crude sample with the direct buffer forming a nucleic acid containing solution; wherein the direct buffer comprises a plurality of primer pairs; wherein each primer pair flanks a genomic locus containing a short tandem repeat (STR); performing PCR on the solution to form a plurality of PCR amplicons; wherein each PCR amplicon has an ascertainable size; and identifying the human by reference to size of the PCR amplicons; wherein the direct buffer further comprises 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% polysorbate, 1000-3000 ug/ml BSA; and 0.101-0.35 U/ul of DNA polymerase.

In some of the embodiments include methods of preparing nucleic acids for a downstream enzymatic manipulation comprising; providing a crude sample comprising: deoxyribonucleic acid; optionally incubating the crude sample with NaOH at 5 mM to 25 mM; mixing the crude sample with a direct buffer to form a nucleic acid containing solution; and performing a downstream enzymatic manipulation on the solution, wherein the direct buffer comprises 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% polysorbate, 1000-3000 ug/ml BSA, and 0.10-0.35 U/ul of DNA polymerase. In some embodiments, the downstream enzymatic manipulation is PCR.

The present teachings also provide kits for genetic analysis, the kits comprising; a plurality of primer pairs, wherein each primer pair flanks a genomic locus containing a short tandem repeat (STR); and a direct buffer, wherein the direct buffer comprises 10-50 mM Tris-HCl (pH 8.3), 30-80 mM KCl, 1.4-2.4 mM $MgCl_2$, 0.01%-0.04% sodium azide, 3%-8% glycerol, 100-350 uM of each dNTPs, 0.2%-0.9% polysorbate, 1000-3000 ug/ml BSA, and 0.10-0.35 U/ul of DNA polymerase. In some embodiments, the kits as set forth above can optionally include NaOH or other strong alkaline compounds, or other agents for cell lysis.

Other embodiments are reaction mixtures comprising; a direct buffer and a plurality of primer pairs, wherein each primer pair flanks a genomic locus containing a short tandem repeat (STR), and wherein the direct buffer comprises 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% polysorbate, 1200-3000 ug/ml BSA, and 0.10-0.35 U/ul of DNA polymerase. In some embodiments, the kits as set forth above can optionally include NaOH or other strong alkaline compounds, or other agents for cell lysis.

BRIEF DESCRIPTION OF THE FIGURES

The skilled artisan will understand that the drawings described below are for illustration purposes only. The drawings are not intended to limit the scope of the present teachings in any way.

FIGS. 3A through 12B are comparative electropherograms of STR profiles from 10 individuals whose blood was spotted onto FTA paper, a punch of which was placed into the direct buffer of the present teachings herein and designated by "A". While the electropherograms designated by "B" represent STR profiles of the same 10 individuals' blood prepared using the PowerPlex 16 HS purification system sold by Promega.

DESCRIPTION OF EXEMPLARY EMBODIMENTS

Figure 1:
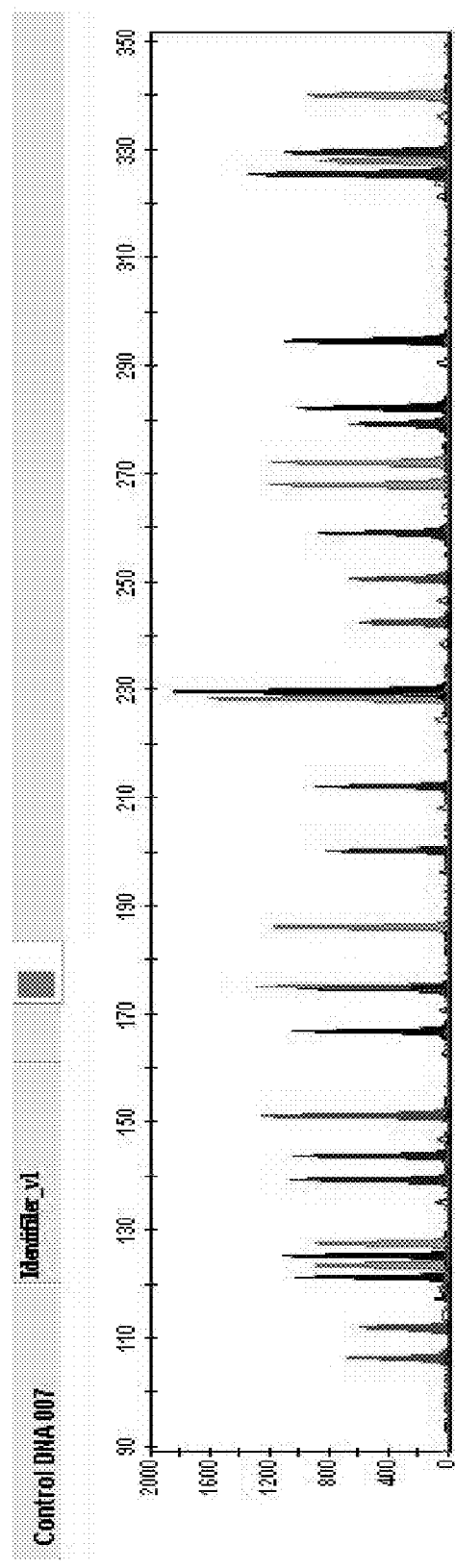
FIG. 1 is an electropherogram of an STR profile of genomic DNA from a blood sample.
Figures 2A, 2B:
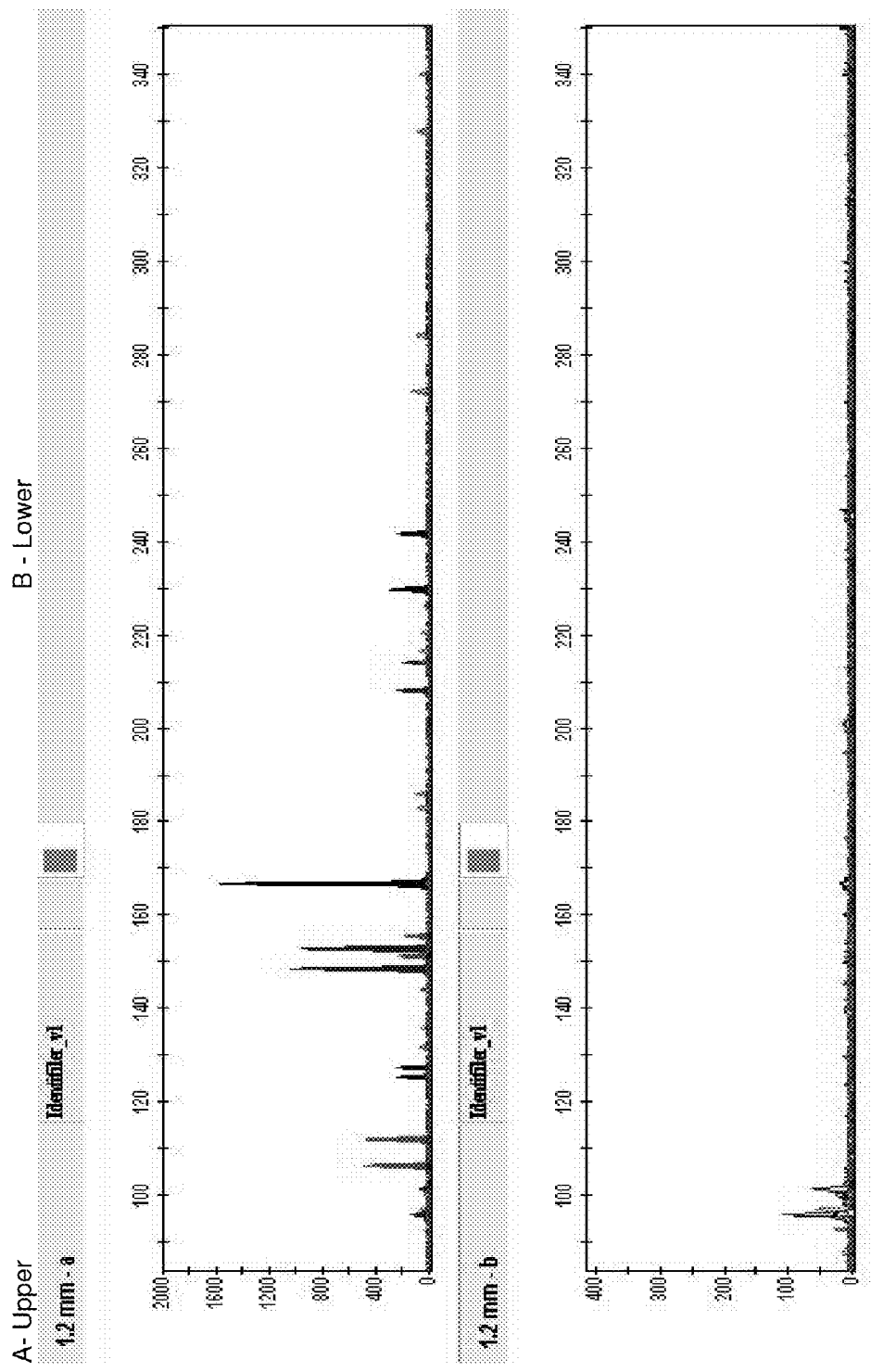
FIGS. 2A-2D are electropherograms of failed STR profiles of four blood samples spotted onto FTA paper.
Figures 2C, 2D:
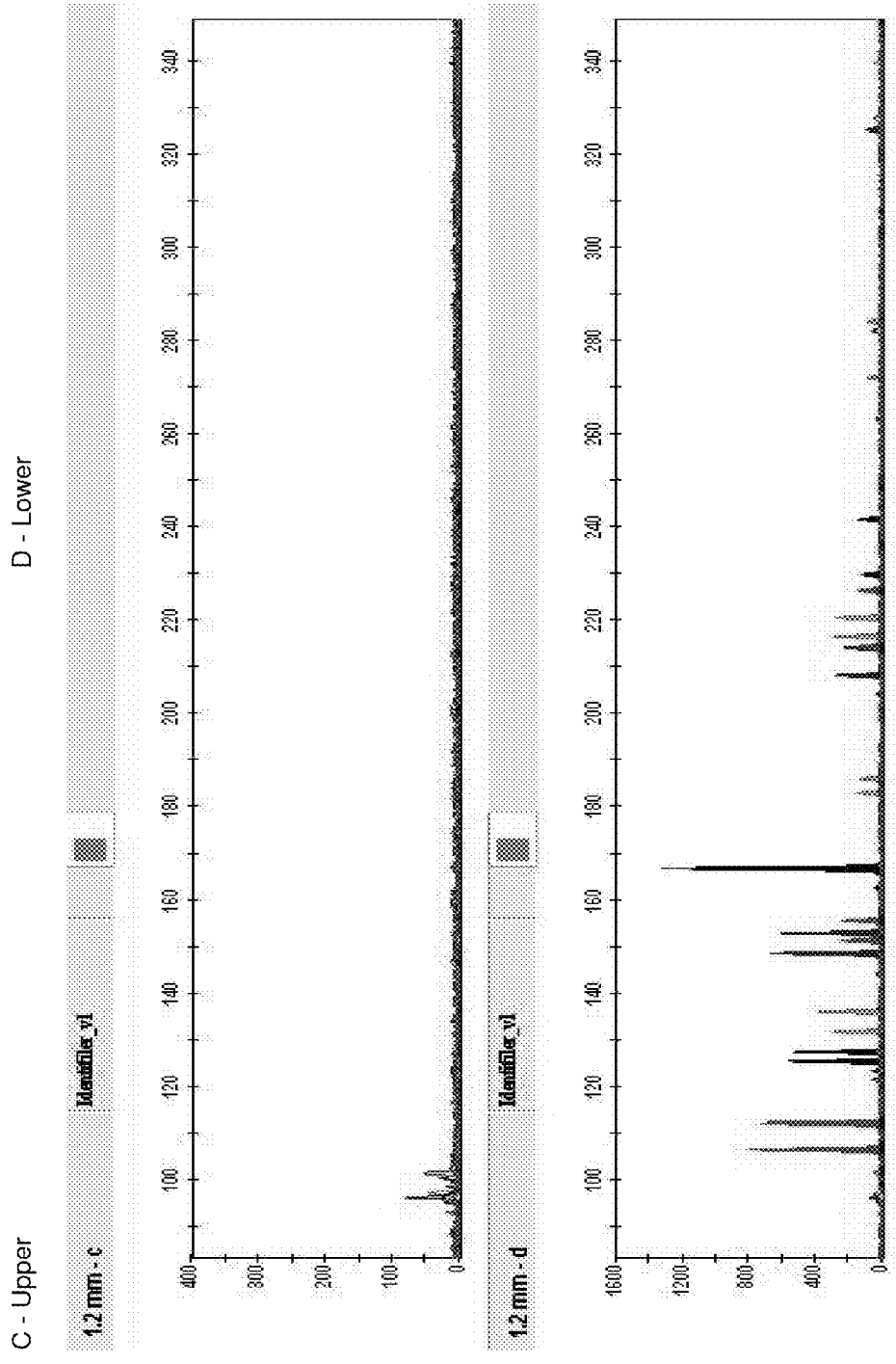
Figures 3A, 3B:
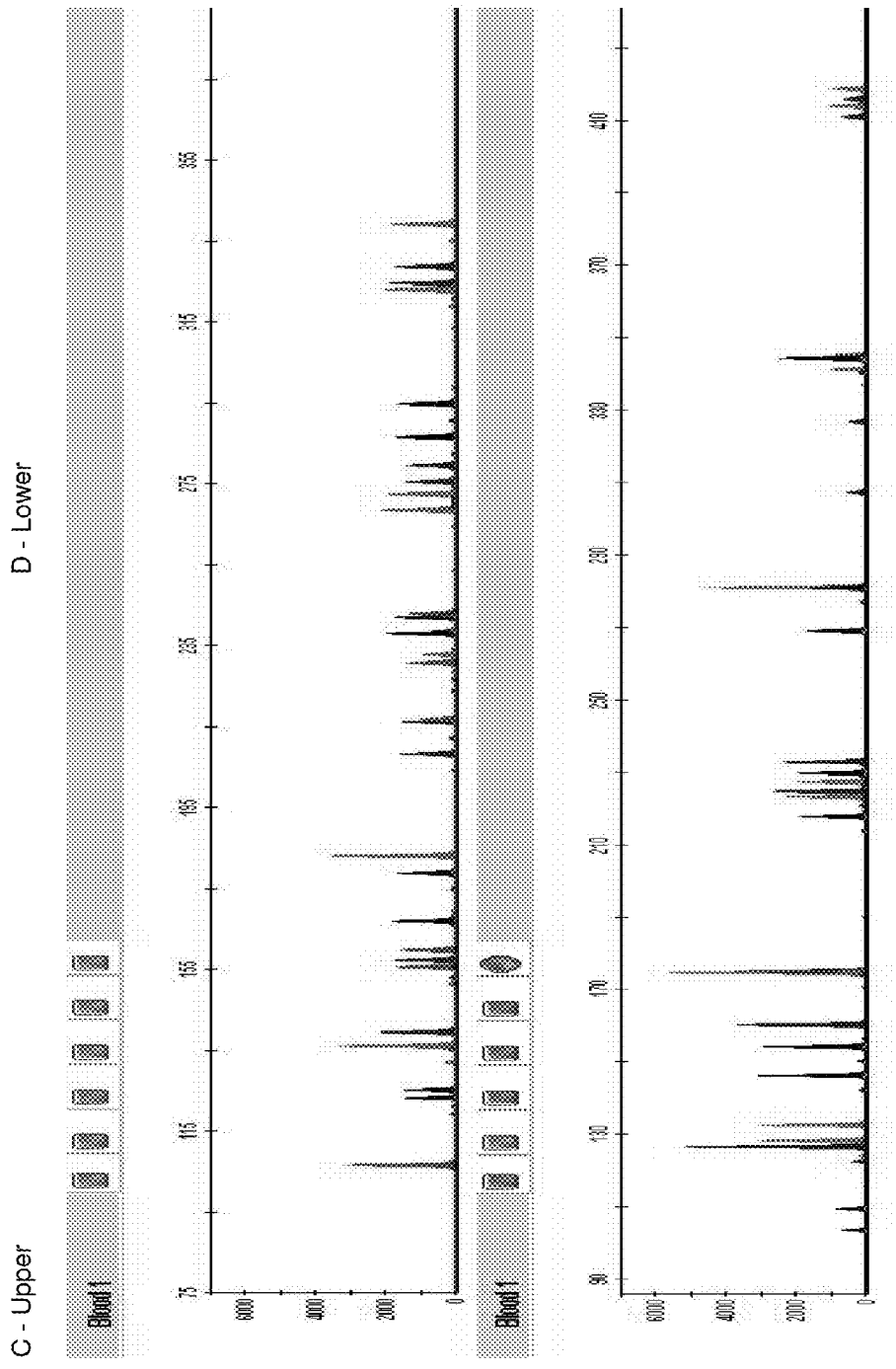
Figures 4A, 4B:
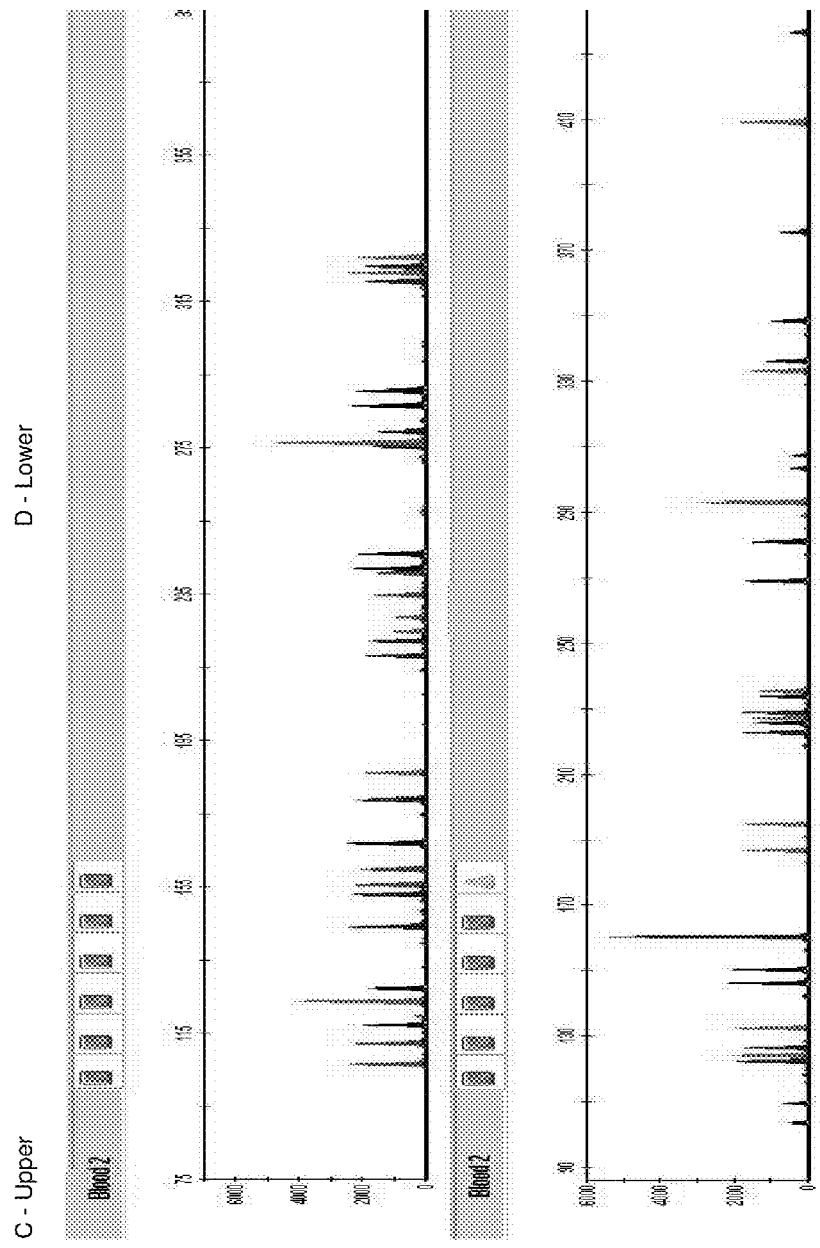
Figures 5A, 5B:
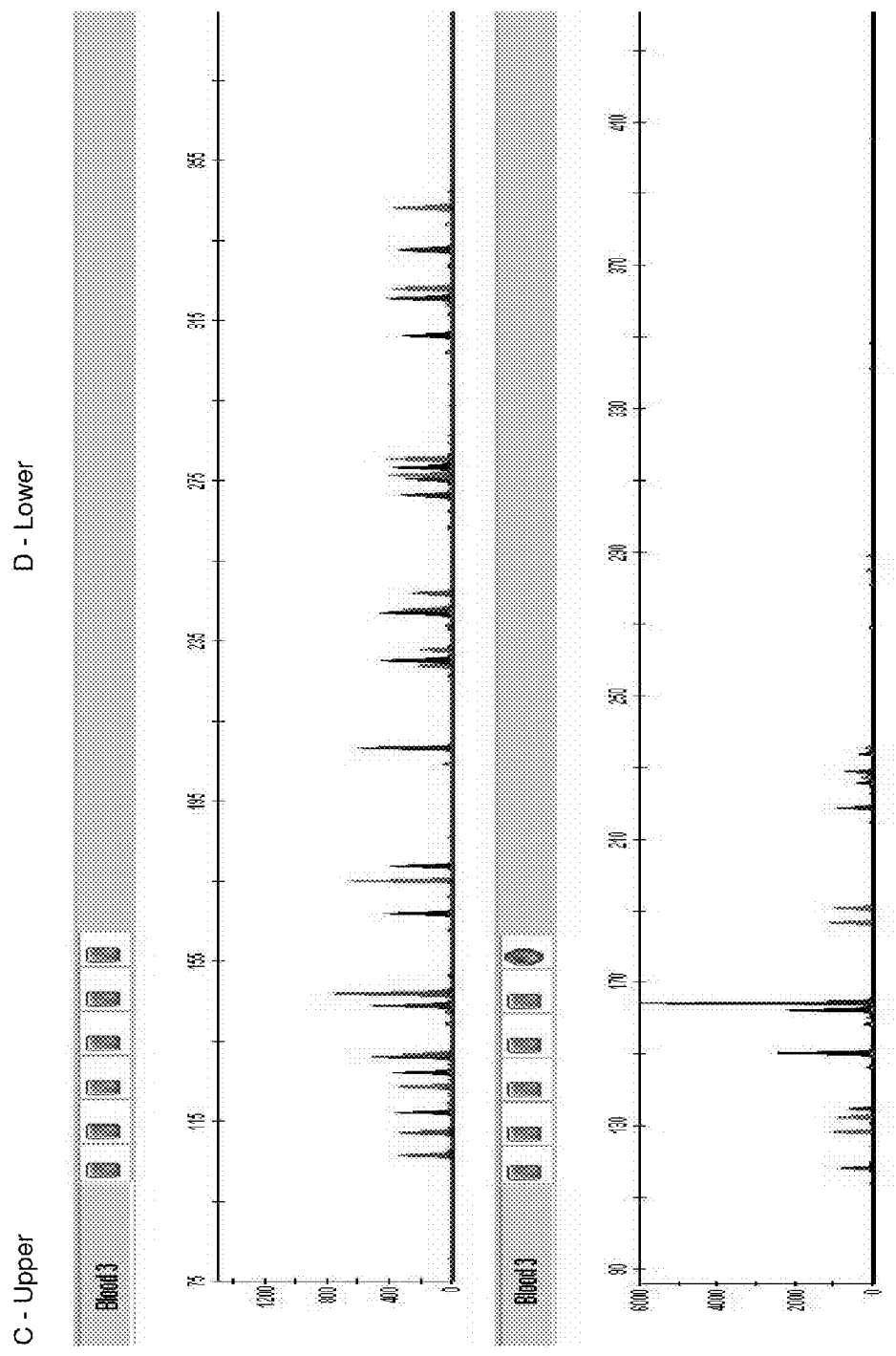
Figure 6A:
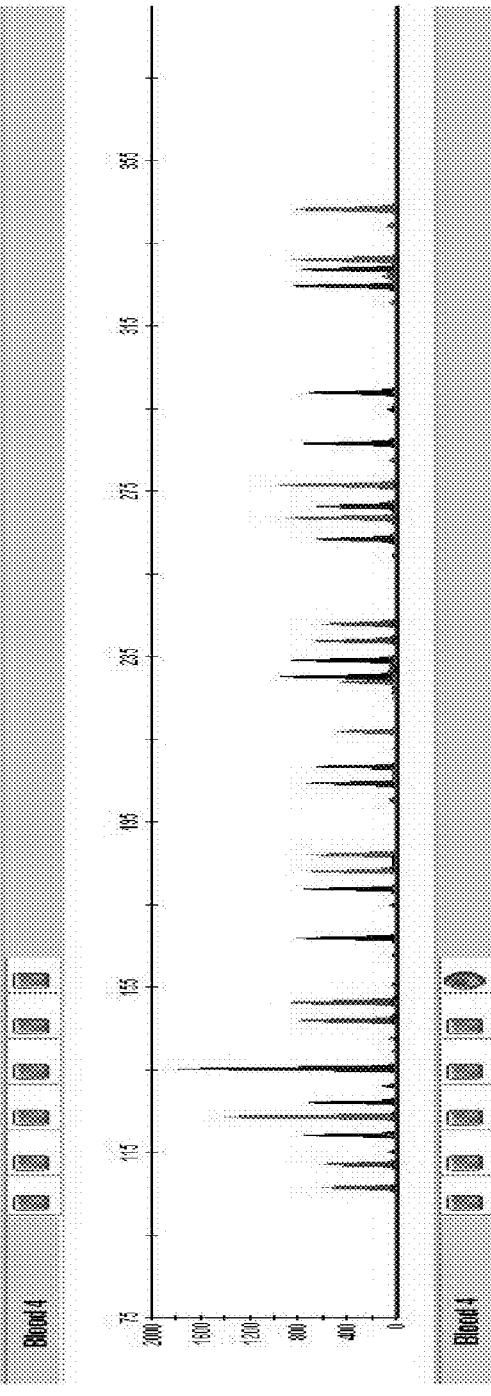
Figure 6B:
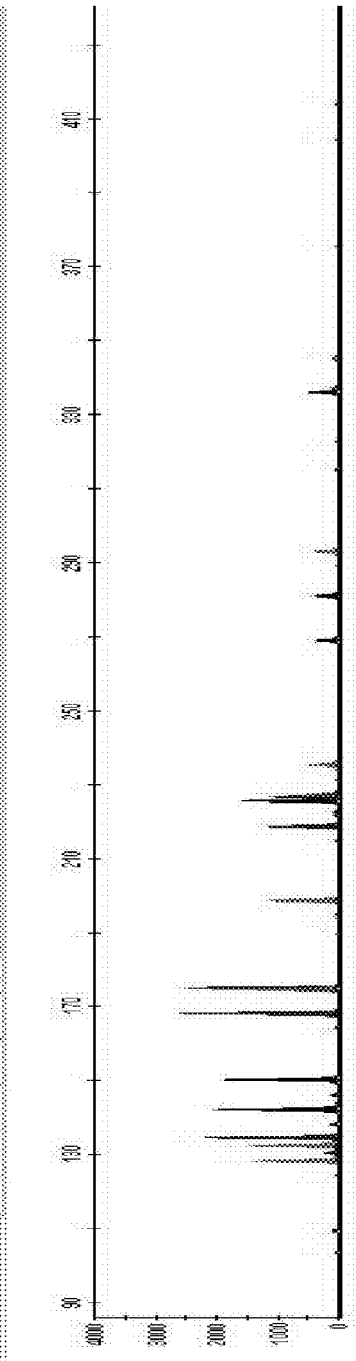
Figures 7A, 7B:
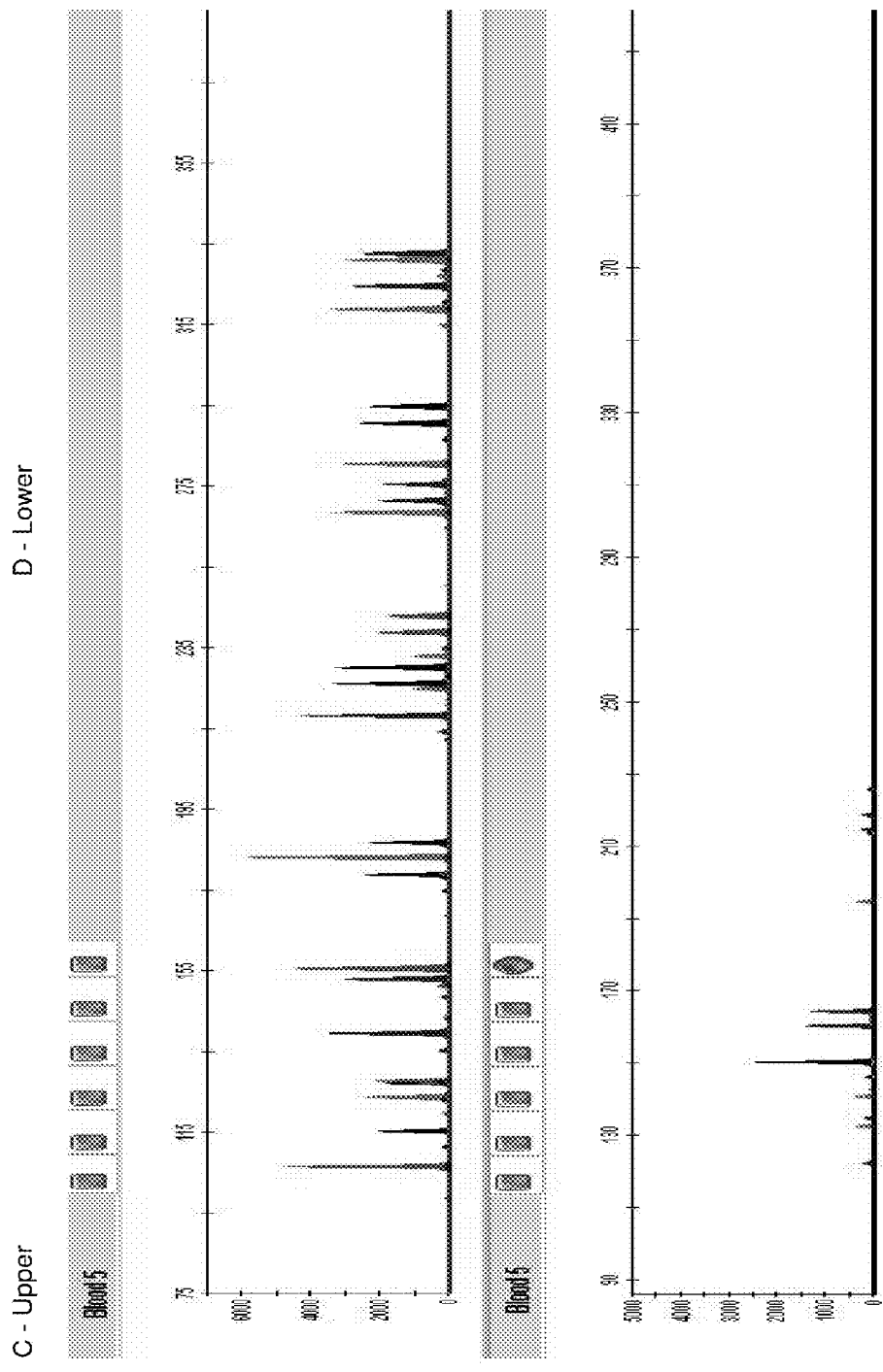
Figures 8A, 8B:
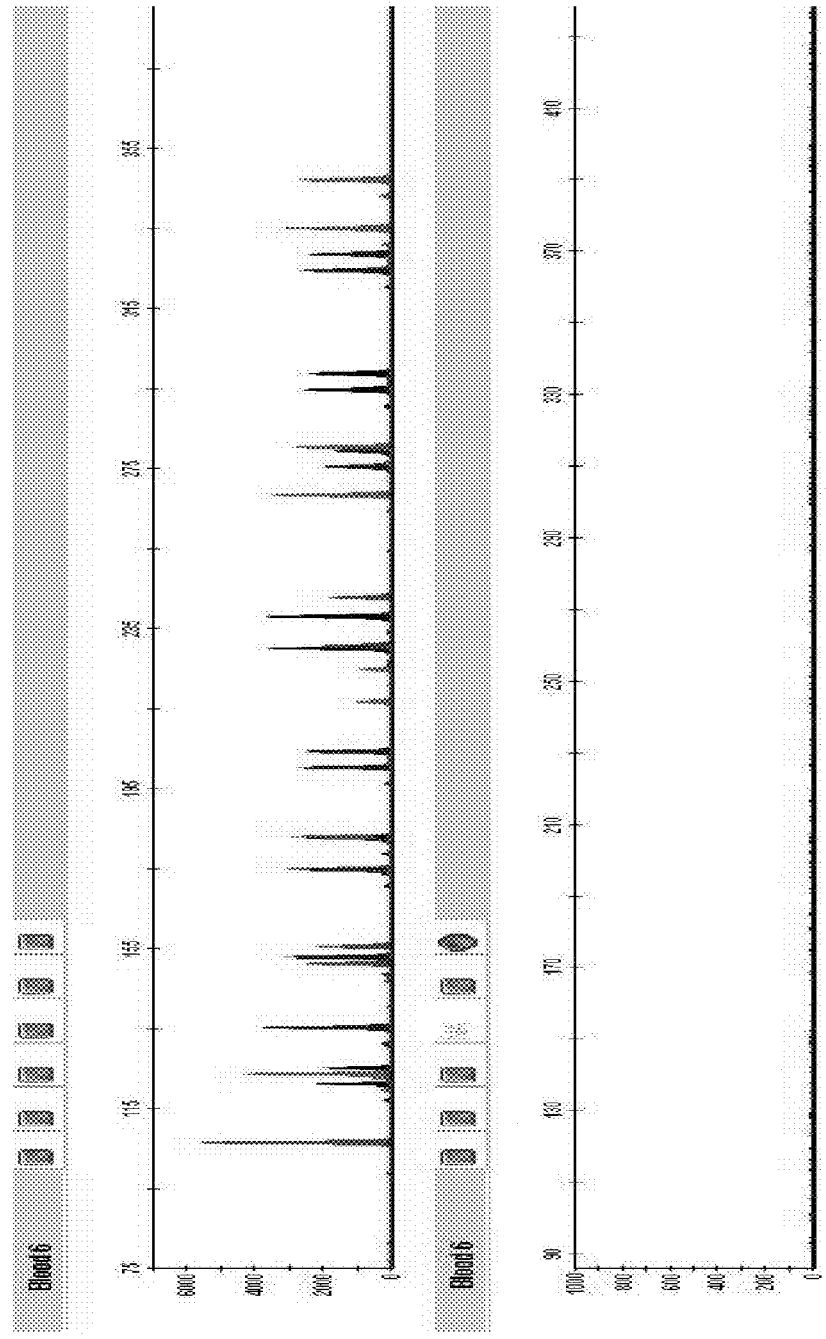
Figures 9A, 9B:
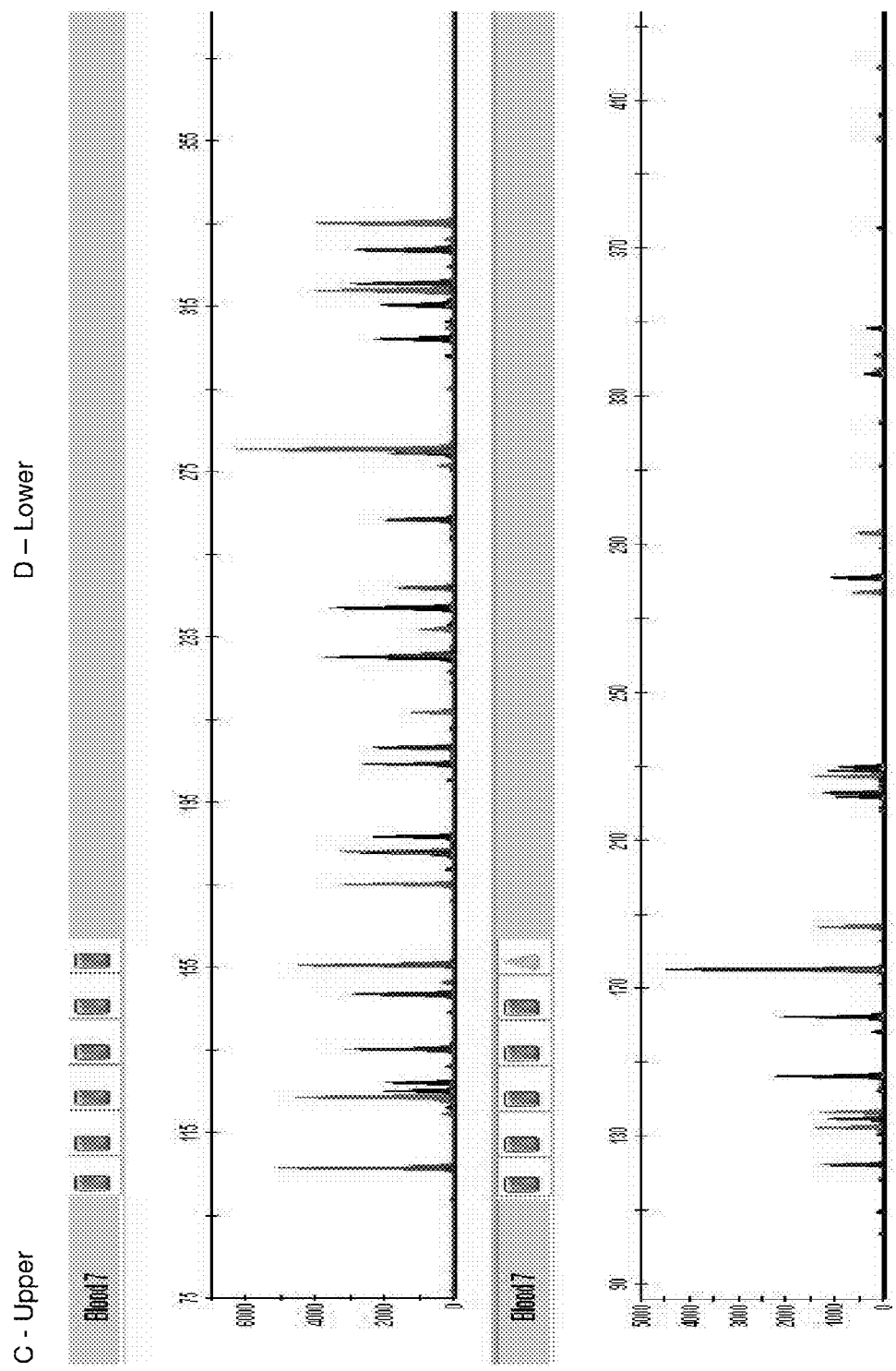
Figures 10A, 10B:
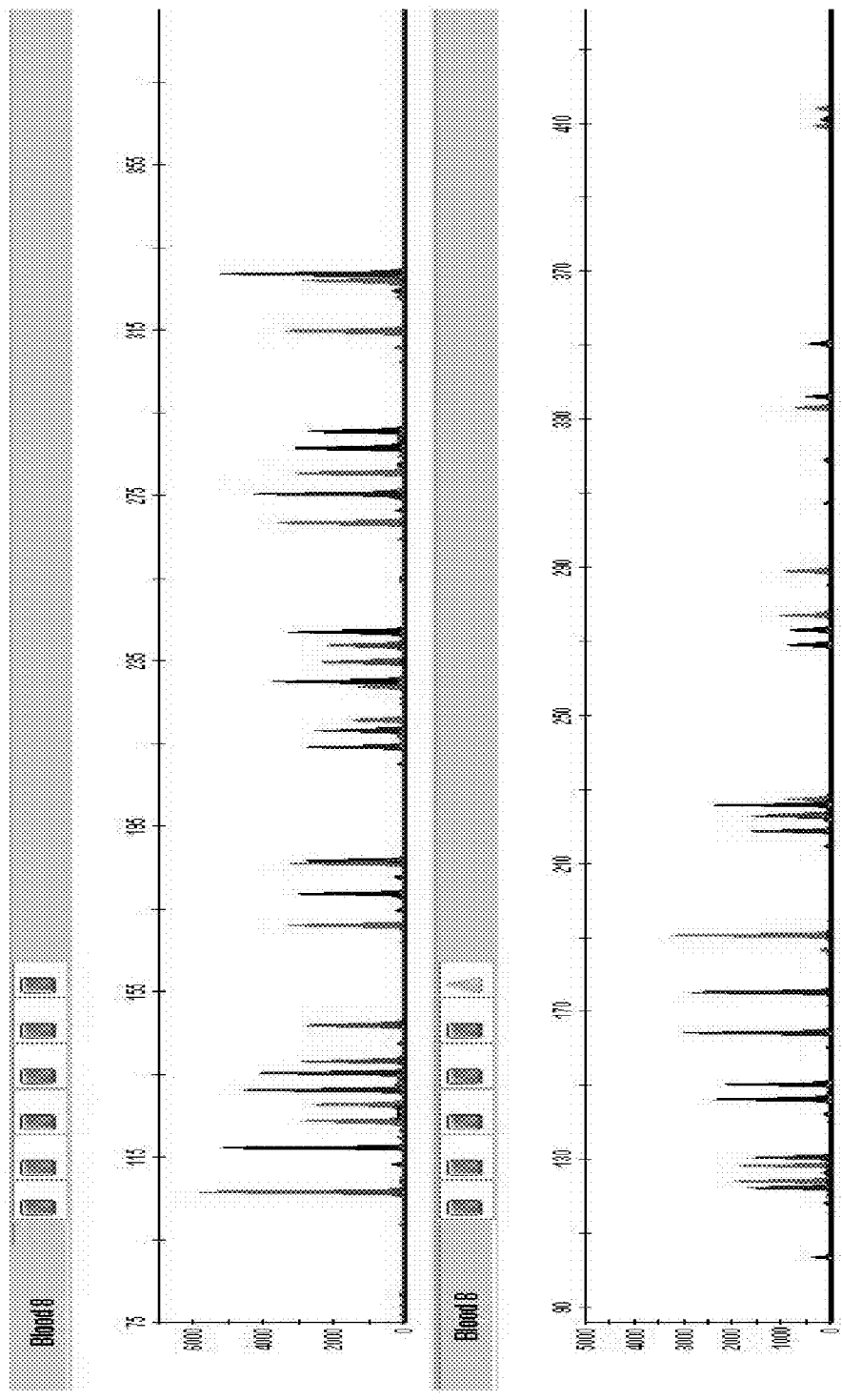
Figures 11A, 11B:
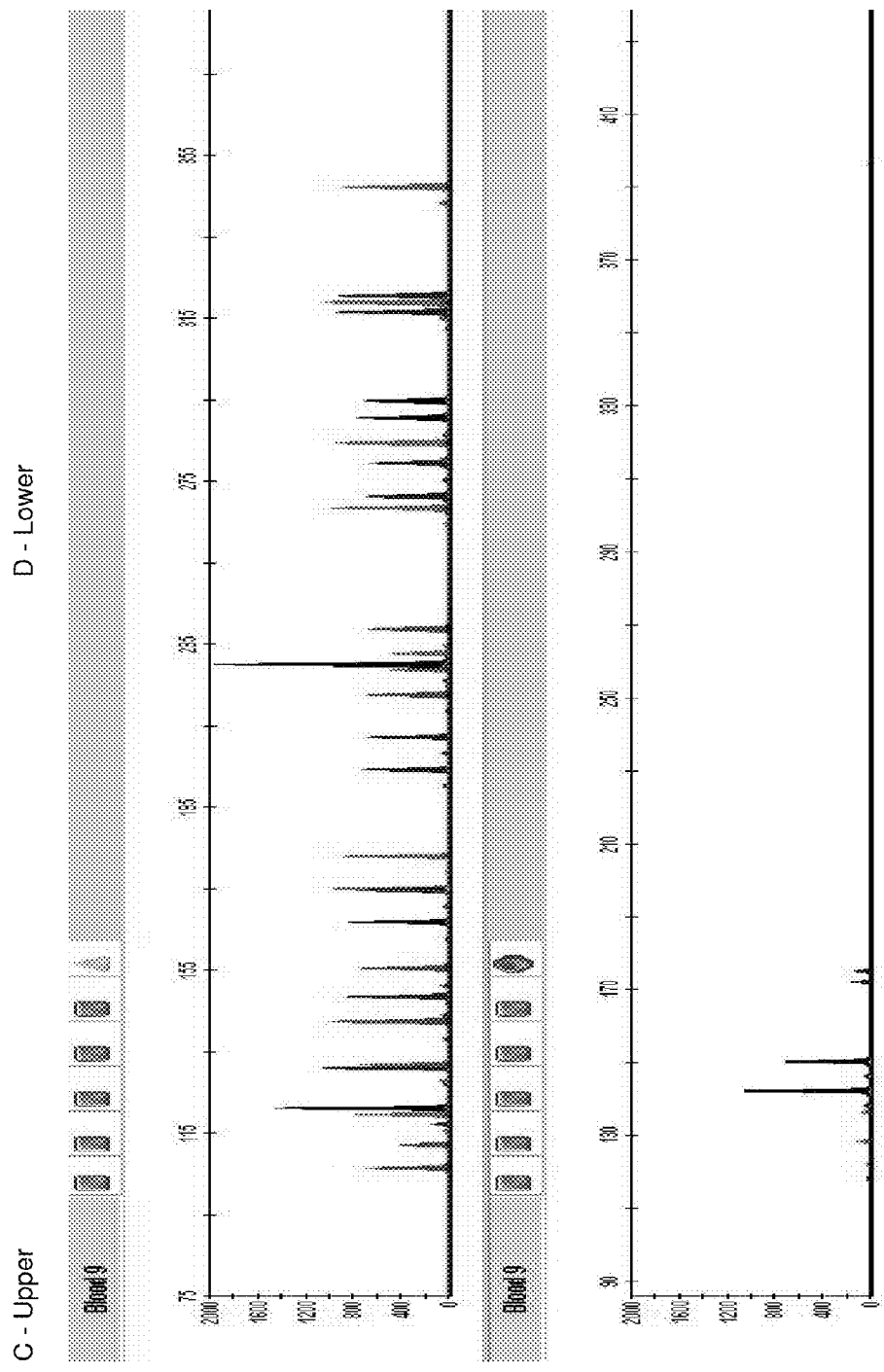
Figures 12A, 12B:
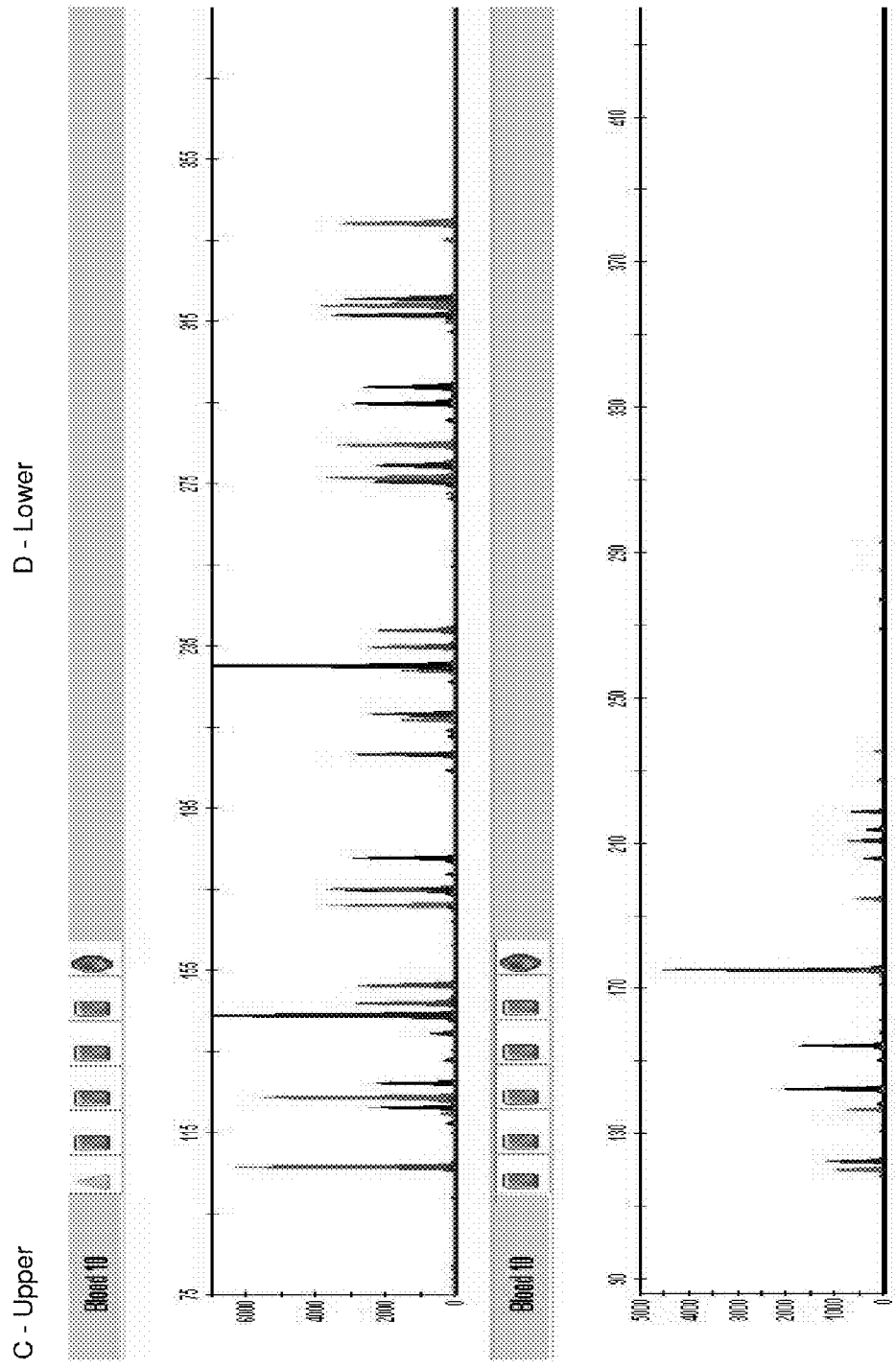

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls.

Some Definitions

As used herein, the term "crude sample" refers to a specimen of biological origin suspected of containing nucleic acids, which has not undergone procedures for the isolation or purification of those nucleic acids. For example, a sample of blood is a crude sample. The cells in crude sample can optionally be lysed. Further, a sample of blood spotted on paper containing a lysis reagent, such as FTA paper (commercially available from Whatman), is a crude sample. A buccal swab of cheek cells is another example of a crude sample. Crude samples include, but are not limited to, blood, diluted blood, blood on paper, buccal swabs, and buccal swabs on a substrate for samples storage, such as FTA paper. One of skill in the art will recognize an enormous variety of other crude samples whose analysis would be facilitated by the present teachings.

As used herein, the term "direct buffer" refers to a buffer into which a crude sample can be placed. The direct buffer contains primers and enzyme for performing a downstream enzymatic manipulation, such as a polymerase chain reaction (PCR). The direct buffer allows for the liberation of the nucleic acids and for their amplification directly in the direct buffer, without the need for any nucleic acid isolation or purification. Illustrative cycling times and temperatures for PCR can be found in Sambrook et al., Molecular Cloning, 3$^{rd}$ Edition 1993. While the present teachings focus on the use of the direct buffer for PCR, it will be appreciated that one of skill in the art can easily employ the direct buffer of the present teachings as a front-end procedure for other types of downstream enzymatic manipulations, for example reverse transcription using a reverse transcriptase, or an oligonucleotide ligation assay using a ligase.

As used herein, "downstream" when used in reference to methods and manipulations performed on a target nucleic acids refers to methods and manipulations performed on a target nucleic acid sample subsequent to a method for liberating a nucleic acid from a biological sample, including, but not limited to, lysis of a cell to release the nucleic acid from the cell.

As used herein, "downstream enzymatic manipulation" refers to procedures performed on a nucleic acid sample, including, but not limited to PCR using a polymerase, reverse transcription using a reverse transcriptase, or an oligonucleotide ligation assay using a ligase.

The term "strong alkaline compound" as used herein includes, but is not limited to, NaOH. Strong alkaline compounds can be used to lyse cells prior to the addition of some embodiments of direct buffer.

As used herein, the term "genomic DNA" refers to the chromosomal DNA sequence of a gene or segment of a gene, including the DNA sequences of non-coding as well as coding regions. Genomic DNA also refers to DNA isolated directly from cells or chromosomes or the cloned copies of all or part of such DNA.

The term "allele" as used herein refers to a genetic variation associated with a gene or a segment of DNA, i.e., one of two or more alternate forms of a DNA sequence occupying the same locus.

The term "locus" as used herein refers to a specific position on a chromosome or a nucleic acid molecule. Alleles of a locus are located at identical sites on homologous chromosomes.

As used herein, the term "short tandem repeat (STR) locus" refers to any region of the human genome which contains short, repetitive sequence elements of 3 to 7 base pairs in length.

As used herein, the term "genomic locus containing a short tandem repeat (STR)" refers to an STR locus in which the number of repetitive sequence elements (and net length of sequence) in a particular region of genomic DNA varies from allele to allele, and from individual to individual.

As used herein, the term "amplification primer" and "primer" refers to an oligonucleotide, which is capable of site—specifically annealing to an RNA or DNA region adjacent a target sequence, and serving as an initiation primer for DNA synthesis under suitable conditions in which synthesis of a primer extension product is induced, e.g., in the presence of nucleotides and a polymerization-inducing agent such as a DNA-dependent DNA polymerase and at suitable temperature, pH, metal concentration, and salt concentration. Typically, a PCR reaction employs a pair of amplification primers also known as "primer pairs" including an "upstream" or "forward" primer and a "downstream" or "reverse" primer, which delimit a region of the RNA or DNA to be amplified.

As used herein, the term "amplifying" refers to a process whereby a portion of a nucleic acid is replicated using, for example, any of a broad range of primer extension reactions. Exemplary primer extension reactions include, but are not limited to, PCR. Unless specifically stated, "amplifying" refers to a single replication or to an arithmetic, logarithmic, or exponential amplification.

The terms "amplicon" and "PCR amplicon" as used herein refers to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other non-limiting examples of amplification include, but are not limited to, ligase detection reaction (LDR) and ligase chain reaction (LCR). Amplification methods can comprise thermal-cycling or can be performed isothermally. In various embodiments, the term "amplification product" includes products from any number of cycles of amplification reactions.

The term "nucleic acid sequence" as used herein can refer to the nucleic acid material itself and is not restricted to the sequence information (i.e. the succession of letters chosen among the five base letters A, C, G, T, or U) that biochemically characterizes a specific nucleic acid, for example, a DNA or RNA molecule.

As used herein, the terms "polynucleotide", "nucleic acid", or "oligonucleotide" refers to a linear polymer of natural or modified monomers or linkages, including deoxyribonucleic acid, deoxyribonucleosides, ribonucleosides, polyamide nucleic acids, and the like, joined by inter-nucleosidic linkages and have the capability of specifically binding to a target polynucleotide by way of a regular pattern of monomer-to-monomer interactions, such as Watson-Crick type of base pairing, and capable of being ligated to another oligonucleotide in a template-driven reaction. Usually monomers are linked by phosphodiester bonds or analogs thereof to form oligonucleotides ranging in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides comprising the bases, as is standard in the art. In naturally occurring polynucleotides, the inter-nucleoside linkage is typically a phosphodiester bond, and the subunits are referred to as "nucleotides."

As used herein "sequence determination", "determining a nucleotide base sequence", "sequencing", identifying and like terms includes determination of partial as well as full sequence information. That is, the term includes sequence comparisons, fingerprinting, and like levels of information about a target polynucleotide, as well as the express identification and ordering of each nucleoside of the target polynucleotide within a region of interest. In certain embodiments, "sequence determination" comprises identifying a single nucleotide, while in other embodiments more than one nucleotide is identified. Identification of nucleosides, nucleotides, and/or bases are considered equivalent herein. It is noted that performing sequence determination on a polynucleotide typically yields equivalent information regarding the sequence of a perfectly complementary polynucleotide and thus is equivalent to sequence determination performed directly on a perfectly complementary polynucleotide.

As used herein, "plurality" in reference to oligonucleotide probes includes sets of two or more oligonucleotide probes where there may be a single "common" oligonucleotide probe that is usually specific for a non-variable region of a target polynucleotide and one or more "wild-type" and/or "mutant" oligonucleotide probes that are usually specific for a region of a target polynucleotide that contains allelic or mutational variants in sequence.

As used herein, "Nucleic acid polymerase" or "polymerase" refers to any polypeptide that catalyzes the synthesis of a polynucleotide using an existing polynucleotide as a template.

As used herein, "DNA polymerase" refers to a nucleic acid polymerase that catalyzes the synthesis of DNA using an existing polynucleotide as a template.

DETAILED DESCRIPTION

A large number of experiments were performed, varying the respective concentration of each of the ingredients of a desired direct buffer, including Tris-HCl, KCl, dNTPs, BSA, AmpliTaq Gold DNA polymerase, $MgCl_2$, and single stranded binding protein (SSB), glycerol, and non-ionic surfactant. These experiments used, for example, humic acid as a representative for the inhibitors typically present in difficult to analyze samples of biological material, and hence served as an easy to produce proxy for crude samples. The results of these experiments indicated that the following formulations were particularly effective in producing high quality results when the samples were analyzed to identify STR alleles.

The present teachings include direct buffers comprising 3%-8% glycerol, 0.2%-0.9% non-ionic surfactants, and 1200-3000 ug/ml BSA.

The present teachings include a direct buffers comprising 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% non-ionic surfactants, 1200-3000 ug/ml BSA, and 0.101-0.35 U/ul of DNA polymerase.

In some embodiments, the non-ionic surfactants can be polysorbate (Tween, Tween 20), Triton-X 100 and the like.

The reagents used in the direct buffer are readily available from commercial suppliers. For example, DNA polymerase is commercially available from Applied Biosystems. Suitable DNA polymerases include Pol A, Pol B, Pol C, Pol D, Pol X, and Pol Y DNA polymerases and a Type I, Type II and Type III DNA polymerase. Generally, thermostable DNA polymerases such as Taq, Pfu, Vent™ DeepVent™, 9° North™, are used in PCR. The DNA polymerases may be modified so as to be inactive prior to subsequent treatment, e.g. heat; for example see U.S. Pat. No. 5,773,258 (chemically modified DNA polymerases), U.S. Pat. No. 5,338,671 antibody bound DNA polymerases. DNA polymerases are known to those skilled in the art. DNA polymerases include DNA-dependent polymerases, which use DNA as a template, or RNA-dependent polymerases, such as reverse transcriptase, which use RNA as a template.

Based on sequence homology, bacterial DNA polymerases can be subdivided into seven different families: A, B, C, D, X, Y, and RT. DNA-dependent DNA polymerases fall into one of six families (A, B, C, D, X, and Y), with most falling into one of three families (A, B, and C). See, e.g., Ito et al. (1991) Nucleic Acids Res. 19:4045-4057; Braithwaite et al. (1993) Nucleic Acids Res. 21:787-802; Filee et al. (2002) J. Mol. Evol. 54:763-773; and Alba (2001) Genome Biol. 2:3002.1-3002.4. Certain DNA polymerases may be single-chain polypeptides (e.g., certain family A and B polymerases) or multi-subunit enzymes (e.g., certain family C polymerases) with one of the subunits having polymerase activity. Id. A fusion protein may comprise a DNA polymerase selected from a family A, B, C, D, X, or Y polymerase.

Family A polymerases ("Pol A") include both replicative and repair polymerases. Replicative members from this family include T7 DNA polymerase and the eukaryotic mitochondrial DNA Polymerase γ. Among the repair polymerases are *E. coli* DNA Pol I, *Thermus aquaticus* Pol I (Taq DNA polymerase), and *Bacillus stearothermophilus* Pol I. Excision repair and processing of Okazaki fragments generated during lagging strand synthesis are performed by the repair polymerases Because most thermostable Pol A enzymes do not possess the 3' to 5' exonuclease activity, they are incapable of proofreading the newly synthesized nucleic acid strand and consequently have high error rates.

Family B polymerases ("Pol B") are substantially replicative polymerases including the major eukaryotic DNA polymerases α, δ, ε, and also DNA polymerase ζ. Pol B polymerases also include DNA polymerases encoded by some bacteria and bacteriophages, of which the best characterized are from T4, Phi29 and RB69 bacteriophages. Pol B enzymes are involved in both leading and lagging strand synthesis and are noteworthy for their remarkable accuracy during replication as many have strong 3'-5' exonuclease activity the exceptions being DNA polymerase α and ζ which lack proofreading activity.

BSA is commercially available from a variety of sources, for example catalog number 10711454001 from Roche. FTA paper is commercially available from Whatman. In some embodiments, FTA paper is used herein with bloodstains. For example, Bloodstain Card from Whatman (Cat# WB 10 0014).

In some embodiments, the FTA paper containing blood or buccal cells is cut out to remove a small region containing biological material, e.g., a circular punch of 0.5 mm to 1.2 mm in diameter, or 1.0-1.5 mm in diameter, or 1.5-2.0 mm in diameter.

In some embodiments, the paper is placed directly into the PCR mix comprising the direct buffer for PCR reaction. In some embodiments, a wash of the FTA paper is not required before placing the FTA paper in the direct buffer.

In some embodiments, when the cells are not initially lysed, e.g., when non-FTA paper is used, a NaOH solution at 5-25 mM is incubated with non-FTA before mixing with the direct buffer and performing a PCR reaction. In other embodiments, the cells may be lysed by exposure to reagents other than NaOH.

In some embodiments, the direct buffer further comprises a plurality of PCR primer pairs. For example, in some embodiments, the direct buffer comprises 5 primer pairs. In some embodiments, the direct buffer comprises 10 primer pairs. In some embodiments, the direct buffer comprises greater than 10 primer pairs. In some embodiments, the direct buffer does not comprise PCR primer pairs, but rather the PCR primer pairs are added at a separate time.

Some embodiments of the subject methods eliminate the need for a sample purification procedure prior to performing PCR. The same protocol can be applied to both blood and buccal cell samples on FTA cards. In addition, the physical sample handling is significantly reduced, therefore this can prevent possible cross-contamination between samples as well as eliminate the possibility of human errors. In some embodiments the amount of time required from FTA card to STR profiles can be reduced by at least 1½ hours. The method is compatible with the current automation instruments available in the forensic market. The costs associated with the purification of DNA from FTA can be eliminated. The success rate of getting a full STR profile is comparable when compared to the traditional standard sample preparation method.

As shown in FIG. 1, a sample of genomic DNA used directly with the Applied Biosystems Identifiler HID v.1 Kit provides a full STR profile. However, the STR profile is either partial or undetectable when blood from genomic DNA is taken from blood spotted on an FTA disc punch (1.2 mm punch) without washing the disc to remove materials which interfere with subsequent sample testing, e.g., STR profiling via direct PCR, see FIGS. 2A-2D.

Further comparative data between the claimed invention and a commercially available product from another reveals in all cases that the direct buffer of the claimed invention provides a full STR profile by direct PCR in 10 out of 10 blood samples spotted on FTA paper using a 1.2 mm size punch (specifically, FIGS. 3-12, electropherograms labeled "A"). Full STR profiles were seen with another's STR kit in only four out of 10 samples tested (FIGS. 3B, 4B, 7B and 8B), partial STR profiles in five of the 10 samples tested (FIGS. 5B-7B and 9B-10B) and no STR profile in one sample (FIG. 6B).

EXAMPLES

In a first example, blood was applied to FTA paper (Whatman) and air-dried. A 0.5 mm disc punch from the FTA paper was made and placed into the direct buffer containing PCR primers from the commercially available Identifiler® Human Identity Kit (Applied Biosystems). PCR was then performed.

In a second example, 100-fold dilutions of blood were made with TE buffer (10 mM Tris-Cl and 0.1 mM EDTA at pH 8.0). 1 ul of diluted blood was used to set up a PCR in the direct buffer.

In a third example, buccal swab samples were collected and placed in 500 ul TE buffer. The resulting suspension was heated at 97° C. for 5 minutes. 10 ul of the resulting suspension was used to set up a PCR in the direct buffer.

Exemplary Kits in Accordance with Some Embodiments of the Present Teachings

The present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

While the present teachings have been described in terms of these exemplary embodiments and experimental data, the skilled artisan will readily understand that numerous variations and modifications of these exemplary embodiments are possible without undue experimentation. All such variations and modifications are within the scope of the current teachings.

Thus, in some embodiments, the present teachings provide a kit comprising; a plurality of primer pairs, wherein each primer pair flanks a genomic locus containing a short tandem repeat (STR); and a direct buffer, wherein the direct buffer comprises 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% non-ionic surfactants, 1200-3000 ug/ml BSA, and 0.10-0.35 U/ul of AmpliTaq Gold DNA polymerase.

Such a kit can be used, for example, in the identification of an organism such as a human by the collection of polymorphic microsatellites analyzed, using for example capillary electrophoresis. Illustrative procedures for performing such human identification can be found for example in the Identifiler HID kit, commercially available from Applied Biosystems, as well as U.S. Pat. Nos. 6,221,598, 6,479,235, 5,843,660, and 7,008,771. In some embodiments, the kits, methods and reaction mixtures provided by the present teachings can be used with procedures for multiplexed PCR of degraded samples, as found for example in WO05054515 to Dimsoski and Woo.

In some embodiments, the direct buffer in the kit comprises 0.2%-0.9% polysorbate, 3%-8% glycerol, 1200-3000 ug/ml BSA.

In some embodiments, the direct buffer in the kit further comprises 10-50 mM Tris-HCl (pH 8.3), 30-80 mM KCl, 1.4-2.4 mM $MgCl_2$, 0.01%-0.04% Sodium azide, 3%-8% glycerol, 100-350 uM of each dNTPs, 0.2%-0.9% polysorbate, 1200-3000 ug/ml BSA, and 0.10-0.35 U/ul of AmpliTaq Gold DNA polymerase.

In some embodiments, the direct buffer in the kit feature comprises NaOH at 5 mM-25 mM. In some embodiments, the NaOH is supplied in a vial separate from the direct buffer.

All literature and similar materials cited in this application, including but not limited to, patents, patent applications, articles, books, treatises, and internet web pages, regardless of the format of such literature and similar materials, are expressly incorporated by reference in their entirety for any purpose. U.S. Application No. 60/896,668 filed Mar. 23, 2007, U.S. application Ser. No. 11/750,316, filed May 17, 2007, and U.S. application Ser. No. 12/054,174, filed Mar. 24, 2008, are incorporated herein by reference in their entirety for all they contain.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

The invention claimed is:

1. A method comprising providing a paper comprising a lysis reagent spotting blood or collecting buccal cells on the paper comprising the lysis reagent placing the blood on paper or the buccal cells on paper in a direct buffer to form a nucleic acid containing solution and performing a PCR on the nucleic acid containing solution, wherein the direct buffer comprises 0.2%-0.9% polysorbate, 3%-8% glycerol, and 1000-3000 ug/ml BSA.

2. The method according to claim 1, wherein the direct buffer further comprises, 10-50 mM Tris-HCl (pH 8.3), 30-80 mM KCl, 1.4-2.4 mM $MgCl_2$, 0.01%-0.04% Sodium azide, 100-350 uM of each dNTPs, and 0.10-0.35 U/ul of DNA polymerase.

3. The method according to claim 1, wherein polysorbate is polysorbate 20.

4. The method of claim 1, wherein the nucleic acid containing solution further comprises a plurality of primer pairs, wherein the plurality of primer pairs flank a plurality of short tandem repeat loci.

5. The method of claim 1, wherein the paper is Fast Technology for Analysis of nucleic acids (FTA) paper.

* * * * *